United States Patent
Jerrentrup et al.

(10) Patent No.: US 12,258,600 B2
(45) Date of Patent: Mar. 25, 2025

(54) **METHOD FOR THE FERMENTATIVE PRODUCTION OF L-LYSINE USING *C. GLUTAMICUM* STRAINS EXPRESSING MODIFIED GLUCONATE REPRESSOR PROTEINS GntR1 AND GntR2**

(71) Applicant: Evonik Operations GmbH, Essen (DE)

(72) Inventors: Silke Jerrentrup, Bielefeld (DE); Brigitte Bathe, Salzkotten (DE); Kornelia Voß, Antwerp (BE); Frank Jankowitsch, Sassenberg (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/693,613

(22) PCT Filed: Sep. 9, 2022

(86) PCT No.: PCT/EP2022/075068
§ 371 (c)(1),
(2) Date: Mar. 20, 2024

(87) PCT Pub. No.: WO2023/041425
PCT Pub. Date: Mar. 23, 2023

(65) Prior Publication Data
US 2024/0271169 A1  Aug. 15, 2024

(30) Foreign Application Priority Data
Sep. 20, 2021 (EP) .................................... 21197722

(51) Int. Cl.
| C12N 1/21 | (2006.01) |
| C07K 14/34 | (2006.01) |
| C12N 9/12 | (2006.01) |
| C12N 15/77 | (2006.01) |
| C12P 13/08 | (2006.01) |

(52) U.S. Cl.
CPC .............. *C12P 13/08* (2013.01); *C07K 14/34* (2013.01); *C12N 9/1217* (2013.01); *C12Y 207/02004* (2013.01)

(58) Field of Classification Search
None
See application file for complete search history.

(56) References Cited

U.S. PATENT DOCUMENTS

| 5,275,940 A | 1/1994 | Kino et al. |
| 5,279,744 A | 1/1994 | Itoh et al. |
| 5,431,933 A | 7/1995 | Binder et al. |
| 5,688,671 A | 11/1997 | Sugimoto et al. |
| 5,763,230 A | 6/1998 | De Hollander et al. |
| 5,770,409 A | 6/1998 | Pfefferle et al. |
| 5,990,350 A | 11/1999 | Stevens et al. |
| 6,025,169 A | 2/2000 | Nakamura et al. |
| 6,844,176 B1 | 1/2005 | Bathe et al. |
| 6,893,848 B1 | 5/2005 | Yokoi et al. |
| 10,683,511 B2 | 6/2020 | Thierbach et al. |
| 10,689,677 B2 | 6/2020 | Schneider et al. |
| 10,717,999 B2 | 7/2020 | Bekel et al. |
| 10,829,746 B2 | 11/2020 | Schneider et al. |
| 11,198,895 B2 | 12/2021 | Thierbach et al. |
| 2009/0311758 A1 | 12/2009 | Jessberger et al. |
| 2018/0100173 A1* | 4/2018 | Park ..................... C12N 15/77 |
| 2019/0085340 A1 | 3/2019 | Thierbach et al. |
| 2019/0106721 A1 | 4/2019 | Bekel et al. |
| 2019/0185890 A1 | 6/2019 | Voss et al. |
| 2020/0017893 A1 | 1/2020 | Bekel et al. |
| 2020/0032306 A1 | 1/2020 | Schneider et al. |
| 2020/0095622 A1 | 3/2020 | Schneider et al. |
| 2020/0190546 A1 | 6/2020 | Bekel et al. |
| 2020/0231946 A1 | 7/2020 | Schneider et al. |
| 2021/0355515 A1 | 11/2021 | Thierbach et al. |

FOREIGN PATENT DOCUMENTS

| EP | 0841395 | 5/1998 |
| EP | 1108790 | 6/2001 |
| EP | 3287469 | 2/2018 |
| WO | 2008/033001 | 3/2008 |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Blombach et al., "Acetohydroxyacid Synthase, a Novel Target for Improvement of L-Lysine Production by *Corynebacterium glutamicum*", Applied And Environmental Microbiology, vol. 75, No. 2, Jan. 2009, pp. 419-427.
Ikeda et al., "The *Corynebacterium glutamicum* genome: features and impacts on biotechnological processes", Appl Microbiol Biotechnol, vol. 62, May 13, 2003, pp. 99-109.
International Search Report dated Dec. 15, 2022, in PCT/EP2022/075068, 10 pages.
International Preliminary Report on Patentability dated Dec. 13, 2023, in PCT/EP2022/075068, 13 pages.

(Continued)

*Primary Examiner* — David Steadman

(74) *Attorney, Agent, or Firm* — Grüneberg and Myers PLLC

(57) ABSTRACT

*C. glutamicum* strains express modified gluconate repressor proteins GntR1 and GntR2. The *C. glutamicum* strains have an increased ability to produce L-lysine compared with an ability of a wildtype strain. The gluconate repressor protein GntR1 includes an amino acid sequence of SEQ ID NO: 9, where the amino acid Arg in position 102 is replaced by the amino acid Glu. The gluconate repressor protein GntR2 includes SEQ ID NO: 10, and its activity is attenuated compared to the activity of the GntR2 repressor protein of the wild-type strain. A method is developed for the fermentative production of L-lysine using such *C. glutamicum* strains.

8 Claims, No Drawings

Specification includes a Sequence Listing.

(56) References Cited

OTHER PUBLICATIONS

Frunzke et al., "Co-ordinated regulation of gluconate catabolismand glucose uptake in *Corynebacterium glutamicum* by two functionally equivalent transcriptional regulators, GntR1 and GntR2", Molecular Microbiology, vol. 67, No. 2, Jan. 1, 2008, pp. 305-322.

Lindroth et al., "High Performance Liquid Chromatographic Determination of Subpicomole Amounts of Amino Acids by Precolumn Fluorescence Derivatization with o-Phthaldialdehyde", Analytical Chemistry, vol. 51, No. 11, Sep. 1979, pp. 1667-1674.

M. Pátek, "Regulation of Gene Expression", Handbook of *Corynebacterium glutamicum*, edited by Lothar Eggeling and Michael Bott, obtained Oct. 8, 2021, pp. 81-98.

Shaeiwitz et al., "Bioseparation", Ullmann's Encyclopedia of Industrial Chemistry, Wiley-VCH Verlag Gmbh & Co. KGaA Weinheim, 10.1002/14356007.b03_11.pub2, Apr. 15, 2012, pp. 1-22.

Spackman et al., "Automatic Recording Apparatus for Use in the Chromatography of Amino Acids", Analytical Chemistry, vol. 30, No. 7, Jul. 1958, pp. 1190-1206.

Tanaka et al., "Genome-Wide Analysis of the Role of Global Transcriptional Regulator GntR1 in *Corynebacterium glutamicum*", Journal of Bacteriology, vol. 196, No. 18, Sep. 2014, pp. 3249-3258.

Teramoto et al., "Transcriptional regulators of multiple genes involved in carbon metabolism in *Corynebacterium glutamicum*", Journal of Biotechnology, vol. 154, Jan. 26, 2011, pp. 114-125.

Wang et al., "Alterations in the transcription factors GntR1 and RamA enhance the growth and central metabolism of *Corynebacterium glutamicum*", Metabolic Engineering, vol. 48, May 9, 2018, pp. 1-12.

Weintraub et al., "Anti-sense RNA as a molecular tool for genetic analysis", reviews, Jan. 1985, 4 Pages.

Written Opinion dated Dec. 15, 2022, in PCT/EP2022/075068, 8 pages.

U.S. Appl. No. 16/149,285, filed Oct. 2, 2018, 2019/0106721, Bekel et al.

U.S. Appl. No. 16/219,718, filed Dec. 13, 2018, 2019/0185890, Voss et al.

U.S. Appl. No. 16/507,690, filed Jul. 10, 2019, 2020/0017893, Bekel et al.

U.S. Appl. No. 16/517,045, filed Jul. 19, 2019, 2020/0032306, Schneider et al.

\* cited by examiner

METHOD FOR THE FERMENTATIVE PRODUCTION OF L-LYSINE USING C. GLUTAMICUM STRAINS EXPRESSING MODIFIED GLUCONATE REPRESSOR PROTEINS GntR1 AND GntR2

CROSS-REFERENCE TO RELATED APPLICATIONS

This application is a National Stage entry under § 371 of International Application No. PCT/EP2022/075068, filed on Sep. 9, 2022, and which claims the benefit of priority to European Patent Application No. 21197722.8, filed on Sep. 20, 2021. The content of each of these applications is hereby incorporated by reference in its entirety.

REFERENCE TO A SEQUENCE LISTING

The present application is accompanied by a .xml file as a computer readable form containing the sequence listing entitled, "Seq-List-005910USPCT-as-filed.xml", created on Feb. 15, 2024, with a file size of 22,724 bytes, the content of which is hereby incorporated by reference in its entirety.

BACKGROUND OF THE INVENTION

Field of the Invention

The present invention concerns C. glutamicum strains expressing modified gluconate repressor proteins GntR1 and GntR2 and a method for the fermentative production of L-lysine using such C. glutamicum strains.

Description of Related Art

For the mass production of useful products such as amino acids, regulation of glucose uptake and pentose phosphorylation pathway in the Corynebacterium strain is very important (Handbook of Corynebacterium glutamicum. 2005. 215-240). The gluconate repressor (GntR) is an important regulatory protein that regulates carbon flow through glucose uptake and pentose phosphorylation pathways. It is known that two gluconate repressors (GntR1 and GntR2) are found in the Corynebacterium glutamicum strain. GntR1 and GntR2 strongly repress the expression of genes which are related to gluconate metabolism (gntP, gntK, gnd), and weakly repress the expression of the pentose phosphate operon (tkt-tal-zwf-opcA-devB), which is a major part of the pentose phosphorylation pathway. On the other hand, the expression of ptsG which encodes the glucose-specific transporter enzyme II of the glucose phosphotransferase system (PTS) is activated by GntR1 and GntR2 (Frunzke, et al., Molecular Microbiology (2008) 67(2), 305-322).

The nucleotide sequence of the Corynebacterium glutamicum ATCC13032 chromosome (cf. Ikeda and Nakagawa, Applied Microbiology and Biotechnology 62, 99-109(2003) and EP 1108790 A2) is available e.g. at the GenBank data base of the NCBI (National Center for Biotechnology Information, U.S. National Library of Medicine 8600 Rockville Pike, Bethesda MD, 20894 USA) under the accession number NC_003450. The nucleotide sequence of the gluconate repressor gene gntR1 comprising locus_tag NCgl2440 is disclosed at the GenBank data base of the NCBI under the accession number NC_003450. The nucleotide sequence of the gluconate repressor gene gntR2 comprising locus_tag NCgl1650 is disclosed at the GenBank data base of the NCBI under the accession number NC_003450.

Tanaka et al (J Bacteriol. (2014); 196(18):3249-58) reported a genome-wide analysis of the role of the transcriptional regulator GntR1 in C. glutamicum.

Furthermore, Wang et al (Metab. Eng. 2018 July; 48:1-12) describe that alterations in the transcription factors GntR1 and RamA enhance the growth and central metabolism of Corynebacterium glutamicum. Teramoto et al. (Journal of Biotechnology 154 (2011) 114-125) reported a double deletion of the two GntR-type functionally redundant regulator genes in C. glutamicum, gntR1 and gntR2, leading to a significantly lower glucose uptake rate and growth rate as compared to the wild type strain (i.e. ATCC 13032) when grown on glucose as the sole carbon source. Park et al (EP 3287469 A1) describe the favorable effect of an amino acid exchange at position 102 from arginine to cysteine of the amino acid sequence of the gluconate repressor protein GntR1 on L-lysine production in Corynebacterium glutamicum.

SUMMARY OF THE INVENTION

The object of the present invention is to provide a C. glutamicum strain having an improved ability to produce L-lysine and a method for producing L-lysine using such strain.

To achieve the object outlined above novel L-lysine excreting bacteria of the species Corynebacterium glutamicum (C. glutamicum), having the ability to excrete L-lysine are provided, comprising in their chromosome a polynucleotide encoding a polypeptide having the activity of a gluconate repressor protein GntR1 comprising the amino acid sequence of SEQ ID NO:9, wherein the amino acid at position 102 of the amino acid sequence of the polypeptide contains a proteinogenic amino acid different from arginine (Arg) and cysteine (Cys), e.g. aspartic acid (Asp) or glutamic acid (Glu), and whereas the activity of the gluconate repressor protein GntR2 in the L-lysine excreting bacteria of the species Corynebacterium glutamicum is attenuated compared to the activity of the GntR2 repressor protein of the wild-type strain.

The present invention further relates to a method for producing L-lysine by using these bacteria in a fermentative process.

DETAILED DESCRIPTION OF THE INVENTION

In particular, the present invention concerns a C. glutamicum strain having an increased ability to produce L-lysine compared with the ability of the wildtype strain and comprising a gene (gntR1) coding for the gluconate repressor protein GntR1 comprising the amino acid sequence of SEQ ID NO: 9 wherein the amino acid Arg, arginine, in position 102 is replaced by the amino acid Glu, glutamic acid, (GntR1(R102E)) and wherein the activity of the gluconate repressor protein GntR2 comprising SEQ ID NO: 10 is attenuated compared to the activity of the GntR2 repressor protein of the wild-type strain.

Attenuation of the activity of the gluconate repressor protein GntR2 means that the translation of the gene gntR2 coding for the gluconate repressor protein GntR2 results in a GntR2 gene product having a reduced repressor activity compared to the activity of the GntR2 repressor protein found in the C. glutamicum wild type or does not result in a GntR2 gene product having the function of a gluconate repressor anymore. This can be achieved e.g. by mutation of the gntR2 gene or by introduction of oligonucleotide fragments into the gntR2 gene or by partial or complete deletion of the coding sequences of the gntR2 gene, respectively.

According to the present invention, the attenuation of the activity of the gluconate repressor protein GntR2 is achieved by deletion of all or part of a gene encoding the polypeptide,
modification of the expression control region (or expression control sequence) to reduce the expression of the gene encoding the polypeptide,
modification of the gene sequence encoding the polypeptide such that the activity of the polypeptide is eliminated or attenuated (e.g., deletion of one or more nucleobases on the nucleotide sequence of the polypeptide gene to encode a polypeptide that has been modified such that the activity of the polypeptide is eliminated or attenuated;
modification of the nucleotide sequence encoding the initiation codon or 5'-UTR region of the gene transcript encoding the polypeptide,
introduction of an antisense oligonucleotide (e.g. antisense RNA) that complementarily binds to the transcript of the gene encoding the polypeptide,
Addition of a sequence complementary to a Shine-Dalgarno sequence in front of a Shine-Dalgarno sequence of a gene encoding a polypeptide to form a secondary structure that cannot be attached to a ribosome or
addition of a promoter transcribed in the opposite direction to the 3' end of the open reading frame (ORF) of the gene sequence encoding the polypeptide (Reverse transcription engineering, RTE) or
a combination of two or more of these measures.

The deletion of a part or all of the gene encoding the polypeptide may be the removal of the entire polynucleotide encoding the endogenous target polypeptide in the chromosome, replacement with a polynucleotide in which some nucleotides are deleted, or replacement with a marker gene.

The modification of the expression control region (or expression control sequence), deletion, insertion, non-conservative or conservative substitution, or a combination thereof, mutation in the expression control region (or expression control sequence) occurs, or weaker replacement with an active sequence. The expression control region also includes a promoter, an operator sequence, a sequence encoding a ribosome binding site, and a sequence regulating the termination of transcription and translation.

The base sequence modification encoding the start codon or 5'-UTR region of the gene transcript encoding the polypeptide is, for example, a base encoding another start codon having a lower polypeptide expression rate than the intrinsic start codon It may e.g. be substituted with a sequence.

The modification of the amino acid sequence or polynucleotide sequence is a deletion, insertion, non-conservative or conservative substitution of the amino acid sequence of the polypeptide or the polynucleotide sequence encoding the polypeptide to weaken the activity of the polypeptide. Or a combination thereof may result in a mutation in sequence, or replacement with an amino acid sequence or polynucleotide sequence improved to have weaker activity or an amino acid sequence or polynucleotide sequence improved to have no activity. For example, by introducing a mutation in the polynucleotide sequence to form a stop codon, the expression of a gene may be inhibited or attenuated but is not limited thereto.

The introduction of an antisense oligonucleotide (eg, antisense RNA) that complementarily binds to the transcript of the gene encoding the polypeptide is described, for example, in Weintraub, H. et al., Antisense-RNA as a molecular tool. for genetic analysis, Reviews—Trends in Genetics, Vol. 1(1) 1986].

The addition of a sequence complementary to the Shine-Dalgarno sequence in front of the Shine-Dalgarno sequence of the gene encoding the polypeptide to form a secondary structure that cannot be attached to the ribosome is mRNA translation It may make it impossible or slow it down.

The addition of a promoter transcribed in the opposite direction to the 3' end of the open reading frame (ORF) of the gene sequence encoding the polypeptide (Reverse transcription engineering, RTE) is an antisense complementary to the transcript of the gene encoding the polypeptide It may be to attenuate activity by making nucleotides.

Particularly, attenuation of the activity of the gluconate repressor protein GntR2 also comprises complete deletion of the gntR2 gene.

SEQ ID NO: 1 shows the DNA sequence of the gluconate repressor gene gntR1 and SEQ ID NO: 9 shows the amino acid sequence of the gluconate repressor protein GntR1 found in the *C. glutamicum* wild type ATCC 13032 (locus_tag NCgl2440 disclosed at the GenBank data base of the NCBI under the accession number NC_003450).

SEQ ID NO: 2 shows the DNA sequence of the gluconate repressor gene gntR2 and SEQ ID NO: 10 shows the amino acid sequence of the gluconate repressor protein GntR2 found in the *C. glutamicum* wild type ATCC 13032 (locus_tag NCgl1650 disclosed at the GenBank data base of the NCBI under the accession number NC_003450).

The representative wild-type strain (the taxonomic type strain) of *C. glutamicum*, ATCC 13032, can be purchased at the American Type Culture Collection (ATCC) and at the DSMZ-German Collection of Microorganisms and Cell Cultures GmbH under the accession no. DSM 20300.

A multitude of L-lysine excreting strains of the genus *Corynebacterium*, in particular of the species *Corynebacterium glutamicum* were obtained in the art during the past decades starting from strains such as ATCC13032, ATCC14067, ATCC13869 and the like. They were obtained as a result of strain development programs using inter alia methods like classical mutagenesis, selection for antimetabolite resistance as well as amplification and promotor modification of genes of the biosynthetic pathway of the L-amino acid in question by genetic engineering methods. Summaries may be found in L. Eggeling and M. Bott (Handbook of *Corynebacterium glutamicum*, CRC Press, 2005) or H. Yukawa and M. Inui (*Corynebacterium glutamicum* Biology and Biotechnology, Springer Verlag, 2013).

L-lysine excreting strains of the species *Corynebacterium glutamicum* are widely known in the art and can be used for the purpose of the present invention. For example, Blombach et al. (Applied and Environmental Microbiology 75(2), 419-427, 2009) describe strain DM1933. Strain DM1933 was obtained from ATCC13032 by several steps of strain development. Furthermore L-lysine excreting *Corynebacterium glutamicum* strain DSM32514 may be used. Strain DM2031 is a further developed derivative of DM1933 having enhanced L-lysine excretion ability. Other L-lysine excreting *Corynebacterium glutamicum* strains are e. g. described in WO 2008033001 A1 and EP 0841395 A1.

L-lysine excreting strains of the species *Corynebacterium glutamicum* typically contain a polynucleotide coding for a feedback resistant aspartokinase polypeptide variant. A feedback resistant aspartokinase polypeptide variant means an aspartokinase which is less sensitive, or desensitized resp., to inhibition by mixtures of L-lysine and L-threonine, e.g. 10 mM each, or mixtures of the L-lysine analogue S-(2-aminoethyl)-L-cysteine and L-threonine, e.g. 50 mM S-(2-aminoethyl)-L-cysteine and 10 mM L-threonine, when compared to the wild form of the enzyme, which is contained in wild strains like for example ATCC13032, ATCC14067 and ATCC13869. The EC number for aspartokinase is EC 2.7.2.4. Descriptions of polynucleotides of *Corynebacterium glutamicum* encoding a feedback resistant aspartokinase polypeptide variant are for example given in U.S. Pat. Nos. 5,688,671, 6,844,176 and 6,893,848. A summarizing list can be found inter alia in US 20090311758 A1. The symbol used in the art for a gene coding for an aspartokinase polypeptide is lysC. In case the gene codes for a feedback resistant polypeptide variant the art typically uses symbols like lysCfbr with fbr indicating feedback resistance.

The *C. glutamicum* strain according to the present invention further comprises at least one copy of a gene lysC coding for a feedback resistant aspartokinase polypeptide variant.

Preferably, the feedback resistant aspartokinase polypeptide variant comprises the amino acid sequence according to SEQ ID NO: 11. The amino acid sequence according to SEQ ID NO: 11 differs from the amino acid sequence of the wild type aspartokinase polypeptide (in ATCC 13032) in that the amino acid threonine (Thr) at position 311 is replaced by the amino acid isoleucine (Ile).

In a further embodiment the bacteria of the *C. glutamicum* strain according to the invention comprise in their chromosome a polynucleotide (gntR1) encoding an amino acid sequence of a polypeptide having gluconate repressor activity (GntR1), wherein the amino acid arginine at position 102 of the encoded amino acid sequence of SEQ ID NO:9 is substituted by glutamic acid (Glu) and wherein the expression of the gene (gntR2) coding for the gluconate repressor protein GntR2 comprising SEQ ID NO: 10 is attenuated compared to the expression of the gntR2 gene of the wild-type gene. SEQ ID NO:5 shows the amino acid sequence of the gluconate repressor protein GntR1 wherein the amino acid Arg in position 102 of the wildtype sequence shown in SEQ ID NO: 9 is replaced by the amino acid Glu (GntR1_R102E) and SEQ ID NO:4 shows the DNA sequence of the gntR1 gene coding for the gluconate repressor protein GntR1 wherein the amino acid Arg in position 102 of the wildtype sequence shown in SEQ ID NO: 9 is replaced by the amino acid Glu (gntR1_R102E)

In a further embodiment of the present invention the gene (gntR2) coding for the gluconate repressor protein GntR2 comprising SEQ ID NO: 10 is deleted in the bacteria of the strain according to the present invention.

It was found that the *C. glutamicum* bacteria modified according to the invention excreted L-lysine, into a suitable medium under suitable fermentation conditions in an increased manner with respect to e.g. product yield (in g l-lysine/l medium or g L-lysine/g carbon source) as compared to the unmodified bacterium.

Therefore, the present invention also concerns a method for the fermentative production of an L-lysine comprising the steps of cultivating the *C. glutamicum* strain of the present invention and accumulating L-lysine in the medium to form an L-lysine containing fermentation broth.

The term L-lysine, where mentioned herein, in particular in the context of product formation, also comprises their ionic forms and salts, for example L-lysine mono hydrochloride or L-lysine sulfate.

The method according to the present invention may further comprise manufacturing an L-lysine containing product from said fermentation broth or isolating L-lysine from the L-lysine containing fermentation broth.

A fermentation broth means a medium in which a *Corynebacterium glutamicum* of the invention has been cultivated for a certain time and under certain conditions.

A suitable medium used for the production of L-lysine by a fermentative process contains a carbon source, a nitrogen source, a phosphorus source, inorganic ions and other organic compounds as required.

Suitable carbon sources include glucose, fructose, sucrose as well as the corresponding raw materials like starch hydrolysate, molasse or high fructose corn syrup.

As nitrogen source organic nitrogen-containing compounds such as peptones, meat extract, soybean hydrolysates or urea, or inorganic compounds such as ammonium sulphate, ammonium chloride, ammonium phosphate, ammonium carbonate, ammonium nitrate, ammonium gas or aqueous ammonia can be used.

As phosphorus source, phosphoric acid, potassium dihydrogen phosphate or dipotassium hydrogen phosphate or the corresponding sodium-containing salts can be used.

Inorganic ions like potassium, sodium, magnesium, calcium, iron and further trace elements etc. are supplied as salts of sulfuric acid, phosphoric acid or hydrochloric acid.

Other organic compounds essentially means growth factors like vitamins e. g. thiamine or biotin or L-amino acids e. g. L-homoserine.

The media components may be added to the culture in form of a single batch or be fed in during the cultivation in a suitable manner.

During the fermentative process the pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8.0. To control foaming, it is possible to employ antifoam agents such as, for example, fatty acid polyglycol esters. To maintain the stability of plasmids, it is possible to add to the medium suitable selective substances such as, for example, antibiotics. The fermentative process is preferably carried out under aerobic conditions. In order to maintain these conditions, oxygen or oxygen-containing gas mixtures such as, for example air are introduced into the culture. The fermentative process is carried out, where appropriate, at elevated pressure, for example at an elevated pressure of 0.03 to 0.2 MPa. The temperature of the culture is normally from 25° C. to 40° C., preferably from 30° C. to 37° C. In a discontinuous process, the cultivation is continued until an amount of the L-lysine sufficient for being recovered has been formed. The cultivation is then completed. This aim is normally achieved within 10 hours to 160 hours. In continuous processes, longer cultivation times are possible.

Examples of suitable media and culture conditions can be found inter alia in L. Eggeling and M. Bott (Handbook of *Corynebacterium glutamicum*, CRC Press, 2005) and the patent documents U.S. Pat. Nos. 5,770,409, 5,990,350, 5,275,940, 5,763,230 and 6,025,169.

The fermentation broth is removed from the culture vessel or fermentation tank, collected where appropriate, and used for providing a product containing the L-lysine, in liquid or solid form. In the simplest case, the L-lysine-containing fermentation broth itself, which has been removed from the fermentation tank, constitutes the recovered product.

The fermentation broth can subsequently be subjected to partial to complete or virtually complete removal of the water, partial to complete or virtually complete removal of the biomass, the latter being optionally inactivated before removal, partial to complete or virtually complete removal of the organic by-products formed during the fermentative process, and partial to complete or virtually complete removal of the residual components of the medium employed or of the residual input materials which have not been consumed in the fermentative process.

Removal of water can be achieved inter alia by evaporation, using e.g. a falling film evaporator, by reverse osmosis or nanofiltration. The concentrates thus obtained can be further worked up by spray drying or spray granulation. It is likewise possible to dry the fermentation broth directly using spray drying or spray granulation.

Removal of the biomass can be achieved inter alia by centrifugation, filtration or decantation or a combination thereof.

Removal of the organic by-products or removal of residual components of the medium can be achieved inter alia by chromatography, e.g. ion exchange chromatography, treatment with activated carbon or crystallization. In case the organic by-products or residual components of the medium are present in the fermentation broth as solids they can also be removed by inter alia by centrifugation, filtration or decantation or a combination thereof.

General instructions on separation, purification and granulation methods can be found inter alia in the book of R. Ghosh "Principles of Bioseperation Engineering" (World Scientific Publishing, 2006), the book of F. J. Dechow "Seperation and Purification Techniques in Biotechnology" (Noyes Publications, 1989), the article "Bioseparation" of Shaeiwitz et al. (Ullmann's Encyclopedia of Industrial Chemistry, Wiley-VCH, 2012) and the book of P. Serno et al. "Granulieren" (Editio Cantor Verlag, 2007).

A downstream processing scheme for L-lysine products can be found in the article "L-lysine Production" of R. Kelle et al. (L. Eggeling and M. Bott (Handbook of *Corynebacterium glutamicum*, CRC Press, 2005)). U.S. Pat. No. 5,279,744 teaches the manufacturing of a purified L-lysine product by ion exchange chromatography. U.S. Pat. No. 5,431,933 teaches the manufacturing of dry L-amino acid products, e. g. an L-lysine product, containing most of the constituents of the fermentation broth.

Thus, a concentration or purification of the L-lysine is achieved and a product having the desired content of said L-lysine is provided.

Finally, L-lysine may be isolated from the culture broth and crystallized in form of a salt, preferably in form of the hydrochloric acid salt of L-lysine.

Analysis of L-lysine to determine its concentration at one or more time(s) during the fermentation can take place by separating the L-lysine by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthalaldehyde rather than ninhydrin for post-column derivatization. An overview article on ion exchange chromatography can be found in Pickering (LC.GC (Magazine of Chromatographic Science 7(6):484-487 (1989)). It is likewise possible to carry out a pre-column derivatization, for example using ortho-phthalaldehyde or phenyl isothiocyanate, and to fractionate the resulting amino acid derivates by reversed-phase chromatography (RP), preferably in the form of high-performance liquid chromatography (HPLC). A method of this type is described, for example, in Lindroth et al. (Analytical Chemistry 51:1167-1174 (1979)). Detection is carried out photometrically (absorption, fluorescence). A review regarding amino acid analysis can be found inter alia in the textbook "Bioanalytik" by Lottspeich and Zorbas (Spektrum Akademischer Verlag, Heidelberg, Germany 1998).

SHORT DESCRIPTION OF THE SEQUENCES

SEQ ID NO:1 shows the gntR1 wild type DNA sequence (locus_tag NCgl2440 disclosed at the GenBank data base of the NCBI under the accession number NC_003450).

SEQ ID NO:2 shows the gntR2 wild type DNA sequence (locus_tag NCgl1650 disclosed at the GenBank data base of the NCBI under the accession number NC_003450).

SEQ ID NO:3 shows the DNA sequence of the lysC gene coding for a feedback resistant aspartokinase polypeptide variant LysC_T311I.

SEQ ID NO: 4 shows the DNA sequence of the gntR1 gene coding for the gluconate repressor protein GntR1 wherein the amino acid Arg in position 102 of the wildtype sequence shown in SEQ ID NO: 9 is replaced by the amino acid Glu (gntR1_R102E; cf. Examples 2-3).

SEQ ID NO:5 shows the amino acid sequence of the gluconate repressor protein GntR1 wherein the amino acid Arg in position 102 of the wildtype sequence shown in SEQ ID NO: 9 is replaced by the amino acid Glu (GntR1_R102E; cf. Examples 2-3).

SEQ ID NO: 6 shows the DNA sequence of the gntR1 gene coding for the gluconate repressor protein GntR1 wherein the amino acid Arg in position 102 of the wildtype sequence shown in SEQ ID NO: 9 is replaced by the amino acid Cys (cysteine, gntR1_R102C; cf. Examples 4-5).

SEQ ID NO:7 shows the amino acid sequence of the gluconate repressor protein GntR1 wherein the amino acid Arg in position 102 of the wildtype sequence shown in SEQ ID NO: 9 is replaced by the amino acid Cys (GntR1_R102C; cf. Examples 4-5).

SEQ ID NO:8 shows a polynucleotide called delta_gntR2 comprising the upstream sequence (5'-flanking sequence) and the downstream sequence (3'-flanking sequence) of the coding sequence of gntR2 (cf. Example 6).

SEQ ID NO:9 shows the GntR1 wild type amino acid sequence (locus_tag NCgl2440 disclosed at the GenBank data base of the NCBI under the accession number NC_003450).

SEQ ID NO: 10 shows the GntR2 wild type amino acid sequence (locus_tag NCgl1650 disclosed at the GenBank data base of the NCBI under the accession number NC_003450).

SEQ ID NO: 11 shows the amino acid sequence of the feedback resistant aspartokinase polypeptide variant LysC_T311I.

EXPERIMENTAL SECTION

A) Materials and Methods

The molecular biology kits, primers and chemicals used and some details of the methods applied are briefly described herewith.

1. Antibiotics and chemicals a. Kanamycin: Kanamycin solution from Streptomyces kanamyceticus from Sigma Aldrich (St. Louis, USA, Cat. no. K0254).

b. Nalidixic acid: Nalidixic acid sodium salt from Sigma Aldrich (St. Louis, USA, Cat. no. N4382).

c. If not stated otherwise, all chemicals were purchased analytically pure from Merck (Darmstadt, Germany), Sigma Aldrich (St. Louis, USA) or Carl-Roth (Karlsruhe, Germany).

2. Cultivation

If not stated otherwise, all cultivation/incubation procedures were performed as follows herewith:

a. LB broth (MILLER) from Merck (Darmstadt, Germany; Cat. no. 110285) was used to cultivate E. coli strains in liquid medium. The liquid cultures (10 ml liquid medium per 100 ml Erlenmeyer flask with 3 baffles) were incubated in the Infors HT Multitron standard incubator shaker from Infors GmbH (Einsbach, Germany) at 37° C. and 200 rpm.

b. LB agar (MILLER) from Merck (Darmstadt, Germany Cat. no. 110283) was used for cultivation of E. coli strains on agar plates. The agar plates were incubated at 37° C. in an INCU-Line® mini incubator from VWR (Radnor, USA).

c. Brain heart infusion broth (BHI) from Merck (Darmstadt, Germany; Cat. no. 110493) was used to cultivate C. glutamicum strains in liquid medium. The liquid cultures (10 ml liquid medium per 100 ml Erlenmeyer flask with 3 baffles) were incubated in the Infors HT Multitron standard incubator shaker from Infors GmbH (Einsbach, Germany) at 33° C. and 200 rpm.

d. Brain heart agar (BHI-agar) from Merck (Darmstadt, Germany; Cat. no. 113825) was used for cultivation of C. glutamicum strains on agar plates. The agar plates were incubated at 33° C. in an incubator from Heraeus Instruments with Kelvitron® temperature controller (Hanau, Germany).

3. Determining optical density a. The optical density of bacterial suspensions in shake flask cultures was determined at 600 nm (OD600) using the BioPhotometer from Eppendorf AG (Hamburg, Germany).

b. The optical density of bacterial suspensions produced in the Wouter Duetz (WDS) micro fermentation system (24-Well Plates) was determined at 660 nm (OD660) with the GENios™ plate reader from Tecan Group AG (Männedorf, Switzerland).

4. Centrifugation a. Benchtop centrifuge for reaction tubes with a volume up to 2 ml Bacterial suspensions with a maximum volume of 2 ml were caused to sediment using 1 ml or 2 ml reaction tubes (e.g. Eppendorf Tubes® 3810X) using an Eppendorf 5417 R centrifuge (5 min. at 13,000 rpm).

b. Benchtop centrifuge for tubes with a volume up to 50 ml

Bacterial suspensions with a maximum volume of 50 ml were caused to sediment using 15 ml or 50 ml centrifuge tubes (e.g. Falcon™ 50 ml Conical Centrifuge Tubes) using an Eppendorf 5810 R centrifuge for 10 min. at 4,000 rpm.

5. Chemical transformation of E. coli

E. coli K-12 strain S17-1 was used as donor for conjugational transfer of plasmids based on pK18mobsacB from E. coli to C. glutamicum. Strain S17-1 is described by Simon, R. et al. (Bio/Technology 1, 784-794, 1983). It is available from the American Type Culture Collection under the access number ATCC47055.

Chemically competent E. coli S17-1 cells were made as follows: A preculture of 10 ml LB medium (10 ml liquid medium per 100 ml Erlenmeyer flask with 3 baffles) was inoculated with 100 µl bacterial suspension of strain S17-1 and the culture was incubated overnight for about 18 h at 37° C. and 250 rpm. The main culture (70 ml LB contained in a 250 ml Erlenmeyer flask with 3 baffles) was inoculated with 300 µl of the preculture and incubated up to an OD600 of 0.5-0.8 at 37° C. The culture was centrifuged for 6 min. at 4° C. and 4000 rpm and the supernatant was discarded. The cell pellet was resuspended in 20 ml sterile, ice-cold 50 mM $CaCl_2$ solution and incubated on ice for 30 min. After another centrifugation step, the pellet was resuspended in 5 ml ice-cold 50 mM CaCl2 solution and the suspension incubated on ice for 30 min. The cell suspension was then adjusted to a final concentration of 20% glycerol (v/v) with 85% (v/v) sterile ice-cold glycerol. The suspension was divided into 50 µl aliquots and stored at −80° C.

To transform S17-1 cells, the protocol according to Tang et al. (Nucleic Acids Res. 22(14), 2857-2858, 1994) with a heat shock of 45 sec. was used.

6. Conjugation of C. glutamicum

The pK18mobsacB plasmid system described by Schäfer et al. (Gene 145, 69-73, 1994) was used to integrate desired DNA fragments into the chromosome of C. glutamicum. A modified conjugation method of Schäfer et al. (Journal of Bacteriology 172, 1663-1666, 1990) was used to transfer the respective plasmid into the desired C. glutamicum recipient strain.

Liquid cultures of the C. glutamicum strains were carried out in BHI medium at 33° C. The heat shock was carried out at 48.5° C. for 9 min. Transconjugants were selected by plating the conjugation batch on EM8 agar (Table 2), which was supplemented with 25 mg/l kanamycin and 50 mg/l nalidixic acid. The EM8 agar plates were incubated for 72 h at 33° C.

TABLE 1

Composition of the EM8 agar

| Components | Concentration (g/l) |
|---|---|
| Glucose (sterile-filtered) | 23 |
| CSL (corn steep liquor; Roquette; solid content 48 ± 2% w/w) | 30 |
| Peptone from soymeal (Merck, Germany) | 40 |
| $(NH_4)_2SO_4$ | 8 |
| Urea | 3 |
| $KH_2PO_4$ | 4 |
| $MgSO_4·7 H_2O$ | 0.5 |
| $FeSO_4·7 H_2O$ | 0.01 |
| $CuSO_4·5 H_2O$ | 0.001 |
| $ZnSO_4·7 H_2O$ | 0.01 |
| Calcium pantothenate, D(+) | 0.01 |
| Thiamine | 0.001 |
| Inositol | 0.1 |
| Nicotinic acid | 0.001 |
| Biotin (sterile-filtered) | 0.005 |
| $CaCO_3$ (autoclaved separately) | 1.6 |
| Agar-Agar (Merck, Germany) | 14 |

Sterile toothpicks were used to transfer the transconjugants onto BHI agar, which was supplemented with 25 mg/l kanamycin and 50 mg/l nalidixic acid. The agar plates were incubated for 20 h at 33° C. The cultures of the respective transconjugants produced in this manner were then propagated further for 24 h at 33° C. in 10 ml BHI medium contained in 100 ml Erlenmeyer flasks with 3 baffles. An aliquot was taken from the liquid culture suitably diluted and plated (typically 100 to 200 µl) on BHI agar which was supplemented with 10% saccharose. The agar plates were incubated for 48 h at 33° C. The colonies growing on the saccharose containing agar plates were then examined for the phenotype kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Clones that proved to be sensitive to kanamycin and resistant to saccharose were examined for integration of the desired DNA fragment by means of real-time PCR.

7. Glycerol stocks of E. coli and C. glutamicum strains

For long time storage of E. coli- and C. glutamicum strains glycerol stocks were prepared. Selected E. coli clones were cultivated in 10 ml LB medium supplemented with 2 g/l glucose. Selected C. glutamicum clones were cultivated in two-fold concentrated BHI medium supplemented with 2 g/l glucose. Cultures of plasmid containing E. coli strains were supplemented with 50 mg/l kanamycin. Cultures of plasmid containing C. glutamicum strains were supplemented with 25 mg/l kanamycin. The medium was contained in 100 ml Erlenmeyer flasks with 3 baffles. It was inoculated with a loop of cells taken from a colony and the culture incubated for about 18 h at 37° C. and 200 rpm in the case of E. coli and 33° C. and 200 rpm in the case of C. glutamicum. After said incubation period 1.2 ml 85% (v/v) sterile glycerol were added to the culture. The obtained glycerol containing cell suspension was then aliquoted in 2 ml portions and stored at −80° C.

8. Cultivation system according to Wouter Duetz (WDS)

The millilitre-scale cultivation system according to Duetz (Trends Microbiol. 2007; 15(10):469-75) was used to investigate the performance of the C. glutamicum strains constructed. For this purpose, 24-deepwell microplates (24 well WDS plates) from EnzyScreen BV (Heemstede, Netherlands; Cat. no. CR1424), filled with 2.5 mL medium were used.

Precultures of the strains were done in 10 ml two-fold concentrated BHI medium. The medium was contained in a 100 ml Erlenmeyer flask with 3 baffles. It was inoculated with 100 µl of a glycerol stock culture and the culture incubated for 24 h at 33° C. and 200 rpm.

After said incubation period the optical densities OD600 of the precultures were determined. The main cultures were done by inoculating the 2.5 ml medium containing wells of the 24 Well WDS-Plate with an aliquot of the preculture to give an optical density OD600 of 0.1.

As medium for the main culture CGXII medium described by Keilhauer et al. (J. Bacteriol. 1993 September; 175(17): 5595-5603) was used. For convenience the composition of the CGXII medium is shown in table 3.

TABLE 2

Composition of Keilhauer's CGXII medium.

| Components | Concentration (g/l) |
|---|---|
| MOPS (3-(N-Morpholino)propanesulfonic acid) | 42 |
| $(NH_4)_2SO_4$ | 20 |
| Urea | 5 |
| $KH_2PO_4$ | 1 |
| $K_2HPO_4$ | 1 |
| $MgSO_4 \cdot 7\ H_2O$ | 0.25 |
| $CaCl_2$ | 0.01 |
| $FeSO_4 \cdot 7\ H_2O$ | 0.01 |
| $MnSO_4\ H_2O$ | 0.01 |
| $ZnSO_4 \cdot 7\ H_2O$ | 0.001 |
| $CuSO_4 \cdot 5\ H_2O$ | 0.0002 |
| $NiCl_2\ 6\ H_2O$ | 0.00002 |
| Biotin (sterile-filtered) | 0.0002 |
| Protocatechuic acid (sterile-filtered) | 0.03 |
| Carbon source (sterile-filtered) | as needed |
| adjust the pH to 7 with NaOH | |

These main cultures were incubated for approximately 45 h at 33° C. and 300 rpm in an Infors HT Multitron standard incubator shaker from Infors GmbH (Bottmingen, Switzerland) until complete consumption of glucose.

The glucose concentration in the suspension was analysed with the blood glucose-meter OneTouch Vita® from LifeScan (Johnson & Johnson Medical GmbH, Neuss, Germany). After cultivation the culture suspensions were transferred to a deep well microplate. A part of the culture suspension was suitably diluted to measure the OD600. Another part of the culture was centrifuged and the concentration of L-amino acids, in particular L-lysine, and residual glucose were analysed in the supernatant.

9. Amino acid analyser

The concentration of L-lysine and other L-amino acids, e.g. L-valine, in the culture supernatants was determined by ion exchange chromatography using a SYKAM S433 amino acid analyser from SYKAM Vertriebs GmbH (Fürstenfeldbruck, Germany). As solid phase a column with spherical, polystyrene-based cation exchanger (Peek LCA N04/Na, dimension 150×4.6 mm) from SYKAM was used. Depending on the L-amino acid the separation takes place in an isocratic run using a mixture of buffers A and B for elution or by gradient elution using said buffers. As buffer A an aquous solution containing in 20|263 g trisodium citrate, 120 g citric acid, 1100 ml methanol, 100 ml 37% HCl and 2 ml octanoic acid (final pH 3.5) was used. As buffer B an aquous solution containing in 20|392 g trisodium citrate, 100 g boric acidand 2 ml octanoic acid (final pH 10.2) was used. The free amino acids were coloured with ninhydrin through post-column derivatization and detected photometrically at 570 nm.

10. Glucose determination with continuous flow system (CFS)

A SANplus multi-channel continuous flow analyser from SKALAR analytic GmbH (Erkelenz, Germany) was used to determine the concentration of glucose in the supernatant. Glucose was detected with a coupled-enzyme assay (Hexokinase/ Glucose-6-Phosphate-Dehydrogenase) via NADH formation.

B) EXPERIMENTAL RESULTS

Example 1

Sequence of the gntR1 and gntR2 genes of C. glutamicum strain DM1933

Strain DM1933 is an L-lysine producer derived from the C. glutamicum wild type strain ATCC 13032 and has been described by Blombach et al. (Applied and Environmental Microbiology 75(2), 419-427, 2009).

The nucleotide sequence of the chromosome of strain DM1933 was determined by Illumina whole-genome sequencing technology (Illumina Inc., San Diego, CA, US). See e.g. Benjak et al. (2015) Whole-Genome Sequencing for Comparative Genomics and De Novo Genome Assembly. In: Parish T., Roberts D. (eds) Mycobacteria Protocols. Methods in Molecular Biology, Vol 1285. Humana Press, NY, US) and Bennet, S. (Pharmacogenomics 5(4), 433-438, 2004). It was found that the nucleotide sequence of the gntR1 coding sequence (locus_tag NCgl2440) and gntR2 (locus_tag NCgl1650) of strain DM1933 including the nucleotide sequences upstream and downstream thereof are identical to that of ATCC13032 shown in SEQ ID NO:1 and SEQ ID NO:2, respectively.

DM1933 contains in its chromosome a variant of the aspartokinase gene encoding a feedback resistant aspartokinase polypeptide. Said feedback resistant aspartokinase polypeptide has the amino acid sequence of SEQ ID NO:11 of the sequence listing. The amino acid sequence according to SEQ ID NO: 11 differs from the aspartokinase polypeptide amino acid sequence of the C. glutamicum wild type (ATCC 13032) in that the amino acid threonine (Thr) at position 311 is replaced by isoleucine (Ile). In U.S. Pat. No. 7,338,790 the abbreviation "lysC T311I" is used to indicate this exchange. Blombach et al. (Applied and Environmental Microbiology 75(2), 419-427, 2009) use the abbreviation "lysC(T311I)".

Example 2

Construction of plasmid pK18mobsacB_gntR1_R102E

Plasmid pK18mobsacB_gntR1_R102E was constructed to enable incorporation of the mutation causing the amino acid exchange R102E into the nucleotide sequence of the gntR1 coding sequence of strain DM1933. The plasmid is based on the mobilizable vector pK18mobsacB described by Schäfer et al. (Gene 145, 69-73, 1994). For the construction of pK18mobsacB_gntR1_R102E the gntR1_R102E polynucleotide according to SEQ ID NO:4 was synthesized and subcloned into pK18mobsacB by GeneArt (ThermoFisher Scientific (Waltham, USA)).

To assemble the plasmid pK18mobsacB_gntR1_R102E the following steps were done by GeneArt: The two polynucleotides i.e. the vector pK18mobsacB and the polynucleotide gntR1_R102E were both treated with SalI and BamHI, ligated and the ligation mixture used to transform E. coli.

DNA of plasmid pK18mobsacB_gntR1_R102E was isolated from a transformant and the polynucleotide gntR1_R102E created within pK18mobsacB was analyzed by Sanger sequencing.

Example 3

Construction of strain DM1933_gntR1_R102E

The plasmid pK18mobsacB_gntR1_R102E obtained in example 2 was used to incorporate the mutation leading to the amino acid exchange R102E into the chromosome of the L-lysine producer DM1933.

Chemically competent cells of E. coli strain S17-1 were transformed with plasmid DNA of pK18mobsacB_gntR1_R102E. The modified conjugation method of Schäfer et al. (Journal of Bacteriology 172, 1663-1666, 1990) as described in materials and methods was used for conjugal transfer into the strain DM1933 and for selection of transconjugant clones by virtue of their saccharose resistance and kanamycin sensitivity phenotype.

Transconjugant clones in which the gntR1 mutation was introduced were selected according to chromosome sequence analysis, subsequently. The strain in which the gntR1_R102E mutation was introduced was called DM1933_gntR1_R102E. A glycerol stock culture of the transconjugant clone was prepared and used as starting material for further investigations.

Thus, the gntR1 gene of strain DM1933 was mutated with the effect that the amino acid arginine at position 102 of the amino acid sequence of the encoded GntR1 polypeptide was replaced by glutamic acid.

Example 4

Construction of plasmid pK18mobsacB_gntR1_R102C

Plasmid pK18mobsacB_gntR1_R102C was constructed to enable incorporation of the mutation causing the amino acid exchange R102C into the nucleotide sequence of the gntR1 coding sequence of strain DM1933. The plasmid is based on the mobilizable vector pK18mobsacB described by Schäfer et al. (Gene 145, 69-73, 1994). For the construction of pK18mobsacB_gntR1_R102C the gntR1_R102C polynucleotide according to SEQ ID NO:6 was synthesized and subcloned into pK18mobsacB by GeneArt (ThermoFisher Scientific (Waltham, USA)).

To assemble the plasmid pK18mobsacB_gntR1_R102C the following steps were done by GeneArt: The two polynucleotides i.e. the vector pK18mobsacB and the polynucleotide gntR1_R102C were both treated with SalI and BamHI, ligated and the ligation mixture used to transform E. coli.

DNA of plasmid pK18mobsacB_gntR1_R102C was isolated from a transformant and the polynucleotide gntR1_R102C created within pK18mobsacB was analyzed by Sanger sequencing.

Example 5

Construction of strain DM1933_gntR1_R102C

The plasmid pK18mobsacB_gntR1_R102C obtained in example 4 was used to incorporate the mutation leading to the amino acid exchange R102C into the chromosome of the L-lysine producer DM1933.

Chemically competent cells of E. coli strain S17-1 were transformed with plasmid DNA of pK18mobsacB_gntR1_R102C. The modified conjugation method of Schäfer et al. (Journal of Bacteriology 172, 1663-1666, 1990) as described in materials and methods was used for conjugal transfer into the strain DM1933 and for selection of transconjugant clones by virtue of their saccharose resistance and kanamycin sensitivity phenotype.

Transconjugant clones in which the gntR1 mutation was introduced were selected according to chromosome sequence analysis, subsequently. The strain in which the gntR1_R102C mutation was introduced was called DM1933_gntR1_R102C. A glycerol stock culture of the transconjugant clone was prepared and used as starting material for further investigations.

Thus, the gntR1 gene of strain DM1933 was mutated with the effect that the amino acid arginine at position 102 of the amino acid sequence of the encoded GntR1 polypeptide was replaced by cysteine.

Example 6

Construction of plasmid pK18mobsacB_delta_gntR2

Plasmid pK18mobsacB_delta_gntR2 was constructed to enable incorporation of a deletion comprising the gntR2 coding sequence and the adjoining stop codon into the chromosome of the desired C. glutamicum strains.

For this purpose, a polynucleotide called delta_gntR2 comprising the upstream sequence (5'-flanking sequence) and the downstream sequence (3'-flanking sequence) of the coding sequence of gntR2 was synthesized according to SEQ ID NO:8 and further called delta_gntR2.

The plasmid is based on the mobilizable vector pK18mobsacB described by Schäfer et al. (Gene 145, 69-73, 1994). For the construction of pK18mobsacB_delta_gntR2 the synthesized polynucleotide delta_gntR2 was subcloned into pK18mobsacB by GeneArt (ThermoFisher Scientific (Waltham, USA)).

To assemble the plasmid pK18mobsacB_delta_gntR2 the following steps were done by GeneArt: The two polynucleotides i.e. the vector pK18mobsacB and the polynucleotide delta_gntR2 were both treated with EcoRI and SbfI, ligated and the ligation mixture used to transform E. coli.

DNA of plasmid pK18mobsacB_delta_gntR2 was isolated from a transformant and the polynucleotide delta_gntR2 created within pK18mobsacB was analyzed by Sanger sequencing.

Example 7

Construction of strains DM1933_delta_gntR2, DM1933_gntR1_R102C_delta_gntR2 and strain DM1933_gntR1_R102E_delta_gntR2

The plasmid pK18mobsacB_delta_gntR2 obtained in example 6 was used to incorporate the deletion of the complete gntR2 coding sequence and the adjoining stop codon into the chromosome of the strains DM1933, DM1933_gntR1_R102C and DM1933_gntR1_R102E.

Chemically competent cells of *E. coli* strain S17-1 were transformed with plasmid DNA of pK18mobsacB_delta_gntR2. The modified conjugation method of Schäfer et al. (Journal of Bacteriology 172, 1663-1666, 1990) as described in materials and methods was used for conjugal transfer into the strains DM1933, DM1933_gntR1_R102C and DM1933_gntR1_R102E and for selection of transconjugant clones by virtue of their saccharose resistance and kanamycin sensitivity phenotype.

Transconjugant clones in which the gntR2 deletion were introduced were selected according to chromosome sequence analysis, subsequently. The strains in which the gntR2 deletion were introduced were called DM1933_delta_gntR2, DM1933_gntR1_R102C_delta_gntR2 and strain DM1933_gntR1_R102E_delta_gntR2 respectively. A glycerol stock culture of the transconjugant clones were prepared and used as starting material for further investigations.

Example 8

L-lysine production

Strains DM1933 (reference), DM1933 strains carrying gntR1 mutations and DM1933 strains carrying the gntR2 gene deletion obtained in examples 3, 5 and 7 were analyzed for their ability to produce L-lysine from glucose by batch cultivation using the cultivation system according to Wouter Duetz.

As medium CGXII containing 20 g/l glucose as carbon source and 7.5 g/l CSL was used. The cultures were incubated for 45 h until complete consumption of glucose as confirmed by glucose analysis using blood glucose-meter and the concentrations of L-lysine and the optical density OD660 were determined. The result of the experiment is presented in table 3.

TABLE 3

L-lysine production.

| strain | L-lysine[1] (g/l) | OD660 | $Y_{PS}$ (g/g) |
|---|---|---|---|
| DM1933 | 4.03 | 4.80 | 0.20 |
| DM1933_gntR1_R102C | 4.09 | 4.82 | 0.20 |
| DM1933_gntR1_R102E | 4.16 | 4.77 | 0.21 |
| DM1933_delta gntR2 | 4.23 | 4.68 | 0.21 |
| DM1933_gntR1_R102C_delta gntR2 | 4.23 | 4.53 | 0.21 |
| DM1933_gntR1_R102E_delta gntR2 | 6.13 | 3.77 | 0.31 |

[1] as L-lysine × HCl

Data represent mean values of eight independent cultivations.

The experiment shows that L-lysine production was increased in strain DM1933_gntR1_R102E as compared to the parental strain DM1933 and confirmed this effect with respect to strain DM1933_gntR1_R102C carrying the gntR1_R102C mutation (cf. EP3287469 A1).

The experiment further shows that L-lysine production was also increased in strain DM1933_delta gntR2 as compared to the parental strain DM1933.

The experiment also shows that unexpectedly the L-lysine production was strongly increased in strain DM1933_gntR1_R102E_delta gntR2 as compared to all other strains. In particular, this effect has not been seen by analyzing strain DM1933_gntR1_R102C_delta gntR2 having the combination of the gntR1_R102C mutation and the inactivation of gntR2.

SEQUENCE LISTING

```
Sequence total quantity: 11
SEQ ID NO: 1            moltype = DNA  length = 753
FEATURE                 Location/Qualifiers
misc_feature            1..753
                        note = nucleotide sequence comprising locus_tag NCgl2440
                         disclosed inGenbank NC_003450
source                  1..753
                        mol_type = genomic DNA
                        organism = Corynebacterium glutamicum
SEQUENCE: 1
atgacccag caaacgaaag tcctatgact aatccattag gttctgcccc cacccagcc      60
aagccacttc ttgacagtgt tcttgatgag ctcggtcaag atatcatcag tggcaaggtt   120
gctgtcggag ataccttcaa gctgatggac atcggcgagc gttttggcat ttcccgcaca   180
gtggcacgcg aagcgatgcg cgctttggag cagctcggtc ttgtcgcttc ttcacgtcgc   240
attggcatta ctgttttgcc acaggaagag tgggctgttt ttgataagtc catcattcgc   300
tggcgtctca atgacgaagg tcagcgtgaa ggccagcttc agtctcttac cgagcttcgt   360
attgctattg aaccgattgc cgcgcgcagc gttgctcttc acgcgtcaac cgccgagctc   420
gagaaaatcc gcgcgctcgc aacagagatg cgtcagttgg gtgaatctgg tcagggtgcg   480
tcccagcgct tcctcgaagc ggacgtcact ttccacgagc tcatcttgcg ttattgccac   540
aatgagatgt tcgctgcact gattccgtcg attagcgcgg ttcttgtcgg ccgcaccgag   600
ctcggcctgc agcctgatct gccggcgcac gaggcgctag acaaccacga taagcttgcc   660
gacgcctcc ttaaccgcga cgccgacgcc gcagaaactg cgtcccgaaa catcctcaat   720
gaggtgcgca gcgcgctggg cacgctgaac taa                                 753

SEQ ID NO: 2            moltype = DNA  length = 741
FEATURE                 Location/Qualifiers
misc_feature            1..741
                        note = nucleotide sequence comprising locus_tag NCgl1650
                         disclosed in
```

| source | 1..741 |
| --- | --- |
| | mol_type = genomic DNA |
| | organism = Corynebacterium glutamicum |

SEQUENCE: 2

```
atgtccgcag ctttacctca cacagcagca gatcccgtac acaccacccc agcgaaaccg    60
ctgctcgatc atgtcttaga ttcactagga cgcagcatca tcagtggtga aatggaagcc   120
ggtagcacat tcaaactgca agacatcggt gaaaaattcg gtatctcccg caccgtcgcc   180
agagaagcca tgcgtgcctt agagcaactt gggttggtgg cctcatcgag acgaattggt   240
attacagtgc tctcgcacga gcactgggct gtctttgaca aagccattat tcgctggcgc   300
ctcgaagatg agcgtcaacg tgaacagcaa ctgcagtcac tcaccgaact tcgtattgcc   360
attgaaccaa ttgctgcacg cagtgttgcc cttcatgcat cgagcgcaga gattgctatc   420
atcggtgatc ttgctgcacg aatgcgtaac ctcggtgaag ctggtcgtgg cgcatcacaa   480
gaattcctag acgcagatgt gaaatttcat gagcttattt tgcagtattg ccataatgag   540
atgttcgctg ccatggcacc acccataaaa gctgtactag tcggcgcac cacacttggc   600
cttcaacccg atcgacctgc cgaagaagtc ttggacaatc atgatgctct cgcacacgca   660
ctaagtgttc gtaatgcaga cctcgccgaa aaagcatcca ggagcattct gaatgaggtg   720
cgcgacgcac tgacctcgta a                                              741
```

| SEQ ID NO: 3 | moltype = DNA   length = 1266 |
| --- | --- |
| FEATURE | Location/Qualifiers |
| misc_feature | 1..1266 |
| | note = /note="lysC_T311I"/note="exchange of nucleobase |
| | cytosine (c) at position 932 togive thymine (t). The acc |
| | codon for threonine is altered to atccodon for isoleucine" |
| source | 1..1266 |
| | mol_type = genomic DNA |
| | organism = Corynebacterium glutamicum |

SEQUENCE: 3

```
gtggccctgg tcgtacagaa atatggcggt tcctcgcttg agagtgcgga acgcattaga    60
aacgtcgctg aacggatcgt tgccaccaag aaggctggaa atgatgtcgt ggttgtctgc   120
tccgcaatgg gagacaccac ggatgaactt ctagaacttg cagcggcagt gaatcccgtt   180
ccgcagctc gtgaaatgga tatgctcctg actgctggtg agcgtatttc taacgctctc   240
gtcgccatgg ctattgagtc ccttggcgca gaagcccaat cttcacggg ctctcaggct   300
ggtgtgctca ccaccgagcg ccacggaaac gcacgcattg ttgatgtcac tccaggtcgt   360
gtgcgtgaag cactcgatga gggcaagatc tgcattgttg ctggtttcca gggtgttaat   420
aaagaaaccc gcgatgtcac cacgttgggg cgtggtggtt ctgacaccac tgcagttgcg   480
ttggcagctg ctttgaacgc tgatgtgtgt gagatttact cggacgttga cggtgtgtat   540
accgctgacc cgcgcatcgt tcctaatgca cagaagctgg aaaagctcag cttcgaagaa   600
atgctggaac ttgctgctgt tggctccaag attttggtgc tgcacagtgt tgaatacgct   660
cgtgcattca atgtgccact tcgcgtacgc tcgtctttata gtaatgatcc cggcactttg   720
attgccggct ctatggagga tattcctgtg aagaagcag tccttaccgg tgtcgcaacc   780
gacaagtccg aagccaaagt aaccgttctg ggtatttccg ataagccagg cgaggctgcg   840
aaggttttcc gtgcgttggc tgatgcagaa atcaacatgt acatggttct gcagaacgtc   900
tcttctgtag aagacggcac caccgacatc atcttcacct gccctcgttc cgacggccgc   960
cgcgcgatgg agatcttgaa gaagcttcag gttcagggca actggaccaa tgtgcttac   1020
gacgaccagg tcggcaaagt ctccctcgtg ggtgctggca tgaagtctca cccaggtgtt   1080
accgcagagt tcatggaagc tctgcgcgat gtcaacgtga acatcgaatt gatttccacc   1140
tctgagattc gtatttccgt gctgatccgt gaagatgatc tggatgctgc tgcacgtgtc   1200
ttgcatgagc agttccagct gggcggcgaa gacgaagccg tcgtttatgc aggcaccgga   1260
cgctaa                                                              1266
```

| SEQ ID NO: 4 | moltype = DNA   length = 753 |
| --- | --- |
| FEATURE | Location/Qualifiers |
| misc_feature | 1..753 |
| | note = gntR1_R102E |
| source | 1..753 |
| | mol_type = genomic DNA |
| | organism = Corynebacterium glutamicum |

SEQUENCE: 4

```
atgaccccag caaacgaaag tcctatgact aatccattag ttctgcccc caccccagcc    60
aagccacttc ttgacagtgt tcttgatgag ctcggtcaag atatcatcag tggcaaggtt   120
gctgtcggag ataccttcaa gctgatgaac atcggcgagc gttttggcat tccccgcaca   180
gtggcacgcg aagcgatgcg cgctttggag cagctcggtc ttgtcgcttc ttcacgtcgc   240
attggcatta ctgtttttgcc acaggaagag tgggcgcttc ttgataagtc catcattcgc   300
tgggaactca atgacgaagg tcagcgtgaa ggccagcttc agtctcttac cgagcttcgt   360
attgctattg aaccgattgc cgcgcgcagc gttgctcttc acgcgtcaac cgccgagctc   420
gagaaaatcc gcgcgctcgc aacagagatg cgtcagttgg gtgaatctgg tcagggtgcg   480
tcccagcgct tcctcgaagc ggacgtcact ttccacgagc tcatcttgcg ttattgccac   540
aatgagatgt tcgctgcact gattccgtcg attagccgtg ttcttgtgcg cgaccaggag   600
ctcggcctgc agcctgatct gccggcgcac gaggcgctag acaaccacga taagcttgcc   660
gacgccctcc ttaaccgcga cgccgacgcc cagaaactg cgtcccgaaa catcctcaat   720
gaggtgcgca gcgcgctggg cacgctgaac taa                                 753
```

| SEQ ID NO: 5 | moltype = AA   length = 250 |
| --- | --- |
| FEATURE | Location/Qualifiers |
| REGION | 1..250 |
| | note = gluconate repressor protein variant GntR1_R102E |
| | wherein the aminoacid Arg in position 102 of the wildtype |
| | sequence is replaced bythe amino acid Glu |

```
source                  1..250
                        mol_type = protein
                        organism = Corynebacterium glutamicum
SEQUENCE: 5
MTPANESPMT NPLGSAPTPA KPLLDSVLDE LGQDIISGKV AVGDTFKLMD IGERFGISRT    60
VAREAMRALE QLGLVASSRR IGITVLPQEE WAVFDKSIIR WELNDEGQRE GQLQSLTELR   120
IAIEPIAARS VALHASTAEL EKIRALATEM RQLGESGQGA SQRFLEADVT FHELILRYCH   180
NEMFAALIPS ISAVLVGRTE LGLQPDLPAH EALDNHDKLA DALLNRDADA AETASRNILN   240
EVRSALGTLN                                                         250

SEQ ID NO: 6            moltype = DNA   length = 753
FEATURE                 Location/Qualifiers
misc_feature            1..753
                        note = gntR1_R102C
source                  1..753
                        mol_type = genomic DNA
                        organism = Corynebacterium glutamicum
SEQUENCE: 6
atgaccccag caaacgaaag tcctatgact aatccattag gttctgcccc caccccagcc    60
aagccacttc ttgacagtgt tcttgatgag ctcggtcaag atatcatcag tggcaaggtt   120
gctgtcggag ataccttcaa gctgatggac atcggcgagc gttttggcat ttcccgcaca   180
gtggcacgcg aagcgatgcg cgctttggag cagctcggtc ttgtcgcttc ttcacgtcgc   240
attggcatta ctgtttttgcc acaggaagag tgggctgttt ttgataagtc catcattcgc   300
tggtgtctca atgacgaagg tcagcgtgaa ggccagcttc agtctcttac cgagcttcgt   360
attgctattg aaccgattgc cgcgcgcagc gttgctcttc acgcgtcaac cgccgagctc   420
gagaaaatcc gcgcgctcgc aacagaaatg cgtcagttgg gtgaatctgg tcagggtgcg   480
tcccagcgct tcctcgaagc ggacgtcact ttccacgagc tcatcttgcg ttattgccaa   540
aatgagatgt tcgctgcact gattccgtcg attagcgcgg ttcttgtcgg ccgcaccgag   600
ctcggcctgc agcctgatct gccggcgcac gaggcgctag acaaccacga taagcttgcc   660
gacgccctcc ttaaccgcga cgccgacgcc gcagaaactg cgtcccgaaa catcctcaat   720
gaggtgcgca gcgcgctggg cacgctgaac taa                                753

SEQ ID NO: 7            moltype = AA   length = 250
FEATURE                 Location/Qualifiers
REGION                  1..250
                        note = gluconate repressor protein variant GntR1_R102C
                         wherein the aminoacid Arg in position 102 of the wildtype
                         sequence is replaced bythe amino acid Cys
source                  1..250
                        mol_type = protein
                        organism = Corynebacterium glutamicum
SEQUENCE: 7
MTPANESPMT NPLGSAPTPA KPLLDSVLDE LGQDIISGKV AVGDTFKLMD IGERFGISRT    60
VAREAMRALE QLGLVASSRR IGITVLPQEE WAVFDKSIIR WCLNDEGQRE GQLQSLTELR   120
IAIEPIAARS VALHASTAEL EKIRALATEM RQLGESGQGA SQRFLEADVT FHELILRYCH   180
NEMFAALIPS ISAVLVGRTE LGLQPDLPAH EALDNHDKLA DALLNRDADA AETASRNILN   240
EVRSALGTLN                                                         250

SEQ ID NO: 8            moltype = DNA   length = 1514
FEATURE                 Location/Qualifiers
misc_feature            1..1514
                        note = polynucleotide called delta_gntR2 comprising the
                         upstreamsequence (5-flanking sequence) and the downstream
                         sequence(3-flanking sequence) of the coding sequence of
                         gntR2
source                  1..1514
                        mol_type = other DNA
                        organism = Corynebacterium glutamicum
SEQUENCE: 8
gaattcagat ctagaatcac tgttccagca gctctaccac acagatctac ctgaaccatc    60
catcaaagac agtggtctta tcagtgctat cggctctagc gccggcaata ccaataatcc   120
agcactcgcc ctagaaactc agtggcttta ccacctggtg cttgctatgc accacaccga   180
tgttgctacc tggcacaagg tggtgaccaa aaacatcacc gaatctgctg ctgcacaaga   240
tgctgcggtc gagcacagtg ctaaatacga tgctgtgtac gatgccgcac aacttatggg   300
catcactgtt gaggaaggta atgtcggtag catcgctatt gcctttagca cagcacgtgg   360
agacggtaaa tctgattggt gtgtttccgg catcagccgc tacatcgagg tcaccgaagc   420
cttggatgct gcgcgagctg tcactaaaaa tactgctgcg ctcaataaaa ctgctctacc   480
agacgtgcag ccggcgccgg ttgtgcattc agcacagttc atgaacaagt ccgcacacag   540
tcatggggtt aatactgcgg aaaaagatca accaaccctg ttttaaaaga ctgtccattt   600
aacaaccaca tcgttacccc cgaacagtct tttaaaggct attcagggg1 aatttttcg    660
ccacactccc aatatctacc aaaaatggtg atctattata cataatgaa  ttaccaaagc   720
ttcatatcac ttttccacag cctgaaagaa catactttgc cactaaacga gtcactacac   780
aattacatcg ctcattgtta cttaattacc ctttaatagt cttttacaag gctgttaaag   840
ggtaatttt tattagtttg cttaaagcct attacagca aattacagca caattgaaaa   900
gtcacttaag cgcacgctaa aagcgaattg tagagggtta ttttttttcg aattaaaagc   960
cttttgcgac acaaatagga caacaaaaca aagatgcatt aactctaaaa gaacaaaatt  1020
aatcaatcag aaaaacatat tgaatactta taaatttctg acatactcat taatgagata  1080
ttcgaagtct ttatcaaaat gattaacaaa aggagtatgt ttatgtcgct aaaaactcgc  1140
cgaatattcg gcgcacttgc tgtttcgcta tcaatctctt tctcagccat tgctacacct  1200
```

```
gcagcatccg cacaagaact agtggtgagc acatcagcag taaacgaatt tggtgtagtt   1260
accagtgaca tcacggctga gcaaattctt caggcgcaag atctaatcgc tgagatgaaa   1320
cagtcagagg acatatatga gtatttcggt gccttgtctg acgttgaaca gagatccatc   1380
attgcagctg taaaggaaaa tccatatctc attgagaacg aatcaccccg tatgagagtc   1440
caaagtgaaa cacccgacga ggaaacacct gataagaaaa agccgagcaa aacctacaag   1500
ctctatcctg cagg                                                     1514

SEQ ID NO: 9              moltype = AA  length = 250
FEATURE                   Location/Qualifiers
REGION                    1..250
                          note = GntR1
source                    1..250
                          mol_type = protein
                          organism = Corynebacterium glutamicum
SEQUENCE: 9
MTPANESPMT NPLGSAPTPA KPLLDSVLDE LGQDIISGKV AVGDTFKLMD IGERFGISRT    60
VAREAMRALE QLGLVASSRR IGITVLPQEE WAVFDKSIIR WRLNDEGQRE GQLQSLTELR   120
IAIEPIAARS VALHASTAEL EKIRALATEM RQLGESGQGA SQRFLEADVT FHELILRYCH   180
NEMFAALIPS ISAVLVGRTE LGLQPDLPAH EALDNHDKLA DALLNRDADA AETASRNILN   240
EVRSALGTLN                                                          250

SEQ ID NO: 10             moltype = AA  length = 246
FEATURE                   Location/Qualifiers
REGION                    1..246
                          note = GntR2
source                    1..246
                          mol_type = protein
                          organism = Corynebacterium glutamicum
SEQUENCE: 10
MSAALPHTAA DPVHTTPAKP LLDHVLDSLG RSIISGEMEA GSTFKLQDIG EKFGISRTVA    60
REAMRALEQL GLVASSRRIG ITVLSHEHWA VFDKAIIRWR LEDERQREQQ LQSLTELRIA   120
IEPIAARSVA LHASSAEIAI IGDLAARMRN LGEAGRGASQ EFLDADVKFH ELILQYCHNE   180
MFAAMAPPIK AVLVGRTTLG LQPDRPAEEV LDNHDALAHA LSVRNADLAE KASRSILNEV   240
RDALTS                                                              246

SEQ ID NO: 11             moltype = AA  length = 421
FEATURE                   Location/Qualifiers
REGION                    1..421
                          note = LysC_T311I
source                    1..421
                          mol_type = protein
                          organism = Corynebacterium glutamicum
SEQUENCE: 11
MALVVQKYGG SSLESAERIR NVAERIVATK KAGNDVVVVC SAMGDTTDEL LELAAAVNPV    60
PPAREMDMLL TAGERISNAL VAMAIESLGA EAQSFTGSQA GVLTTERHGN ARIVDVTPGR   120
VREALDEGKI CIVAGFQGVN KETRDVTTLG RGGSDTTAVA LAAALNADVC EIYSDVDGVY   180
TADPRIVPNA QKLEKLSFEE MLELAAVGSK ILVLRSVEYA RAFNVPLRVR SSYSNDPGTL   240
IAGSMEDIPV EEAVLTGVAT DKSEAKVTVL GISDKPGEAA KVFRALADAE INIDMVLQNV   300
SSVEDGTTDI IFTCPRSDGR RAMEILKKLQ VQGNWTNVLY DDQVGKVSLV GAGMKSHPGV   360
TAEFMEALRD VNVNIELIST SEIRISVLIR EDDLDAAARA LHEQFQLGGE DEAVVYAGTG   420
R                                                                   421
```

The invention claimed is:

1. A Corynebacterium glutamicum strain having an increased ability to produce L-lysine compared with an ability of a wildtype strain, comprising:
   a gene coding for a mutant GntR1 protein comprising the amino acid sequence of SEQ ID NO: 9 except for a R102E substitution and
   an inactivated gluconate repressor protein GntR2 gene.

2. The Corynebacterium glutamicum strain of claim 1, further comprising at least one copy of a gene lysC coding for a feedback resistant aspartokinase polypeptide variant.

3. The Corynebacterium glutamicum strain of claim 2, wherein an amino acid sequence of the feedback resistant aspartokinase polypeptide variant comprises SEQ ID NO: 11.

4. The Corynebacterium glutamicum strain of claim 1, comprising in its chromosome a polynucleotide encoding an amino acid sequence of a polypeptide having gluconate repressor activity comprising the amino acid sequence according to SEQ ID NO:5.

5. The Corynebacterium glutamicum strain of claim 1, wherein a gene gntR2 coding for the gluconate repressor protein GntR2 is deleted.

6. A method for a fermentative production of an L-lysine, comprising:
   cultivating the Corynebacterium glutamicum strain of claim 1, and
   accumulating L-lysine in a medium to form an L-lysine containing fermentation broth.

7. The method of claim 6, further comprising:
   manufacturing an L-lysine containing product from said fermentation broth.

8. The method of claim 7, further comprising:
   isolating L-lysine from the L-lysine containing fermentation broth.

* * * * *